(12) United States Patent  
Zhao et al.

(10) Patent No.: US 9,503,713 B2  
(45) Date of Patent: Nov. 22, 2016

(54) METHOD AND SYSTEM FOR STEREO GAZE TRACKING

(71) Applicants: Intuitive Surgical Operations, Inc., Sunnyvale, CA (US); Imperial Innovations Limited, London (GB)

(72) Inventors: Wenyi Zhao, Mountain View, CA (US); Brandon D. Itkowitz, Sunnyvale, CA (US); George Mylonas, London (GB); Gung-Zhong Yang, London (GB)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/662,653

(22) Filed: Oct. 29, 2012

(65) Prior Publication Data

US 2013/0107207 A1     May 2, 2013

Related U.S. Application Data

(60) Provisional application No. 61/554,741, filed on Nov. 2, 2011.

(51) Int. Cl.
| | |
|---|---|
| *A61B 3/14* | (2006.01) |
| *H04N 13/04* | (2006.01) |
| *A61B 3/00* | (2006.01) |

(Continued)

(52) U.S. Cl.  
CPC ......... *H04N 13/0484* (2013.01); *A61B 3/0058* (2013.01); *A61B 3/113* (2013.01); *G06K 9/00604* (2013.01)

(58) Field of Classification Search  
CPC .......... A61B 3/14; A61B 3/12; A61B 3/107; A61B 3/0091; A61B 3/13; A61B 3/145; A61B 3/0083; A61B 3/024; A61B 3/032; A61B 19/5223; A61B 3/00; A61B 5/0073; G06T 2207/30041; G06T 19/00; H04N 5/23212  
USPC ................ 351/205–206, 200, 246, 212, 211; 606/204.25  
See application file for complete search history.

(56) References Cited

U.S. PATENT DOCUMENTS

| | | |
|---|---|---|
| 5,049,147 A | 9/1991 | Danon |
| 5,293,187 A | 3/1994 | Knapp et al. |
| 5,626,595 A | 5/1997 | Sklar et al. |

(Continued)

FOREIGN PATENT DOCUMENTS

| | | |
|---|---|---|
| WO | 2006087689 A2 | 8/2006 |
| WO | 2011125007 A1 | 10/2011 |

OTHER PUBLICATIONS

Gaze Contingent Depth Recovery and Motion Stabilisation for Minimally Invasive Robotic Surgery, G.-Z. Yang and T. Jiang (Eds.): MIAR 2004, LNCS 3150, pp. 311-319, 2004.*

(Continued)

*Primary Examiner* — James Greece  
*Assistant Examiner* — Sharrief Broome

(57) ABSTRACT

Stereo gaze tracking estimates a 3-D gaze point by projecting determined right and left eye gaze points on left and right stereo images. The determined right and left eye gaze points are based on one or more tracked eye gaze points, estimates for non-tracked eye gaze points based upon the tracked gaze points and image matching in the left and right stereo images, and confidence scores indicative of the reliability of the tracked gaze points and/or the image matching.

20 Claims, 12 Drawing Sheets

(51) Int. Cl.
*A61B 3/113* (2006.01)
*G06K 9/00* (2006.01)

(56) References Cited

U.S. PATENT DOCUMENTS

| | | | |
|---|---|---|---|
| 5,800,423 | A | 9/1998 | Jensen |
| 5,817,084 | A | 10/1998 | Jensen |
| 5,844,824 | A | 12/1998 | Newman et al. |
| 5,861,940 | A | 1/1999 | Robinson et al. |
| 5,912,721 | A | 6/1999 | Yamaguchi et al. |
| 5,931,832 | A | 8/1999 | Jensen |
| 6,406,472 | B1 | 6/2002 | Jensen |
| 6,459,446 | B1 | 10/2002 | Harman |
| 6,529,331 | B2 | 3/2003 | Massof et al. |
| 6,578,962 | B1 | 6/2003 | Amir et al. |
| 6,758,843 | B2 | 7/2004 | Jensen |
| 7,108,688 | B2 | 9/2006 | Jensen |
| 7,742,623 | B1 | 6/2010 | Moon et al. |
| 7,773,111 | B2 | 8/2010 | Cleveland et al. |
| 8,155,479 | B2 | 4/2012 | Hoffman et al. |
| 2002/0186348 | A1 | 12/2002 | Covannon et al. |
| 2005/0119638 | A1 | 6/2005 | Jensen |
| 2006/0013473 | A1 | 1/2006 | Woodfill et al. |
| 2006/0100642 | A1 | 5/2006 | Yang et al. |
| 2006/0264915 | A1 | 11/2006 | Jensen |
| 2007/0121068 | A1 | 5/2007 | MacDougall et al. |
| 2008/0181452 | A1 | 7/2008 | Kwon et al. |
| 2009/0163898 | A1* | 6/2009 | Gertner .......... A61B 3/113 606/4 |
| 2009/0248036 | A1* | 10/2009 | Hoffman .......... A61B 1/045 606/130 |
| 2011/0085139 | A1 | 4/2011 | Blixt et al. |
| 2011/0228051 | A1* | 9/2011 | Dedeoglu .......... H04N 13/0022 348/46 |

OTHER PUBLICATIONS

"A Robotic Enhancement System for Endoscopic Surgery," 1994, 83 Pages Total.
"A Robotic Enhancement System for Endoscopic Surgery," 1996, 49 Pages Total.
Actuators for surgical teleoperation, 1995, 12 Pages, SPIE.
Apostoloff, Nicholas et al., "Vision In and Out of Vehicles: Integrated Driver and Road Scene Monitoring," The International Journal of Robotics Research, 2004, pp. 513-538, vol. 23—Issue 4-5, SAGE Publications.
Azuma, Ronald T., "A Survey of Augmented Reality," Teleoperators and Virtual Environments, 1997, pp. 355-385, vol. 6—No. 4.
Bediz, Yusuf and Gozde Bozdagi Akar, "View point tracking for 3D display systems," 13th European Signal Processing Conference (EUSIPCO 2005), Sep. 2005, Turkey, 4 pages, Internet: http://www.eurasip.org/Proceedings/Eusipco/Eusipco2005/defevent/papers/cr1328.pdf.
Beymer, David and Myron Flickner, "Eye Gaze Tracking Using an Active Stereo Head," Proceedings of 2003 IEEE Computer Society Conference on Computer Vision and Pattern Recognition (CVPR '03), Jun. 18-20, 2003, vol. 2, 8 pages.
Burris, Bill, "UCSDs Hospitals Employ a Steady Hand in Surgery," 1993, 1 Page.
Chen J., et al., "3D Gaze Estimation with a Single Camera without IR Illumination," IEEE, Pattern Recognition, 2008. ICPR 2008. 19th International Conference on Dec. 8-11, 2008, pp. 1-4.
Computer Motion, Inc., "AESOP: Automated Endoscopic System for Optimal Positioning," Press Release, 1994, 2 pages.
Darrell, Trevor et al., "Exploring Vision-Based Interfaces: How to Use Your Head in Dual Pointing Tasks," MIT Artificial Intelligence Laboratory AI Memo 2002-001, Jan. 2002, 9 pages, Internet: http://people.csail.mit.edu/aoh/papers/ai_memo.pdf.
Duchowski, Andrew T., "A Breadth-First Survey of Eye Tracking Applications," Behavioral Research Methods, Instruments and Computers, Nov. 2002, vol. 34, Issue4, pp. 455-470.
Ellis, S. R. , "Nature and Origins of Virtual Environments:A Bibliographical Essay," Computing Systems in Engineering, 1991, pp. 321-347, vol. 2—No. 4, Pergamon Press.
Gienko G., et al., "Eye-Tracking in Augmented Photogrammetric Technologies," ASPRS 2005 Annual Conference, Geospatial Goes Global: From Your Neighborhood to the Whole Planet, Mar. 7-11, 2005, 8 pages.
Hutchinson, Thomas E. et al., "Human-Computer Interaction Using Eye-Gaze Input," IEEE Transactions on Systems, Man, and Cybernetics, vol. 19, No. 6, Nov./Dec. 1989, pp. 1527-1534.
Jian-Nan C., et al., "Pupil Tracking Method Based on Particle Filtering in Gaze Tracking System," International Journal of the Physical Sciences, Mar. 4, 2011, vol. 6 (5), pp. 1233-1243.
Kim K.N., et al., "Vision-Based Eye-Gaze Tracking for Human Computer Interface," Systems, Man, and Cybernetics, 1999, IEEE International Conference on 1999, vol. 2, pp. 324-329.
Lu H.C., et al., "Gaze Tracking by Binocular Vision and LBP Features," Pattern Recognition, 2008, 19th International Conference on Dec. 8-11, 2008, pp. 1-4.
Mylonas, George P. and Guang-Zhong Yang, "Eye Tracking and Depth from Vergence," Chapter 8 in Next generation Artificial Vision Systems, Eds. Anil Bharath and Maria Petrou, Artech House Publishers, Jun. 2008, pp. 2-39.
Mylonas, George P. et al., "Gaze-contingent control for minimally invasive robotic Surgery," Computer Aided Surgery, vol. 11, Issue 5, pp. 256-266, Sep. 2006.
Mylonas, George P. et al., "Gaze-contingent Depth Recovery and Motion Stabilisation for Minimally Invasive Robotic Surgery," Medical Imaging and Augmented Reality (MAIR-2004), Lecture Notes in Computer Science, vol. 3150/2004, pp. 311-319, Springer-Verlag, 2004.
"Robotically Enhanced Manipulation," 1993, 27 Pages Total.
Shih S.W., et al., "A Novel Approach to 3-D Gaze Tracking Using Stereo Cameras," Stereo Cameras, IEEE Transactions on Feb. 2004, 27 pages.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.
Talmi, K. and J. Liu, "Eye and Gaze Tracking for Visually Controlled Interactive Stereoscopic Displays," Signal Processing: Image Communication, vol. 14, pp. 799-810, 1999.
Taubes, Gary et al., "Surgery in Cyberspace," Discover magazine, Dec. 1994, vol. 15, issue 12, pp. 85-92.
Uecker, Darrin R. et al., "A Speech-Directed Multi-Modal Man-Machine Interface for Robotically Enhanced Surgery," 1994, pp. 176-183.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wang, Yulun et al., "Robotically Enhanced Surgery," Medicine Meets Virtual Reality II, 1994, pp. 228-232.
Yang, Guang-Zhong et al., "Visual search: psychophysical models and practical applications," Image and Vision Computing, Elsevier, vol. 20, pp. 291-305, 2002.
Zhu Z., et al., "Eye and Gaze Tracking for Interactive Graphic Display," Machine Vision and Applications, 2004, vol. 15 (3), pp. 139-148.
Extended European Search Report for Application No. 2012846020, mailed on May 20, 2015, 6 pages.

* cited by examiner

METHOD AND SYSTEM FOR STEREO GAZE TRACKING

FIELD OF THE INVENTION

The present invention generally relates to gaze tracking and in particular, to a method and system for stereo gaze tracking.

BACKGROUND

Gaze tracking involves the determination and tracking of the gaze or fixation point of a person's eyes on a surface of an object such as the screen of a computer monitor. The gaze point is generally defined as the intersection of the person's line of sight with the surface of the object being viewed. Schematically, this is shown in FIG. 1 where the person's left and right eyes, "C1" and "C2", separated by interocular distance "b", gaze at a gaze point "P" on an object "O".

When the object being viewed is the screen of a computer monitor, gaze tracking may be used for human-computer interaction such as increasing the resolution or size of the region where the user is gazing or using the gaze point as a cursor. Currently available gaze tracking systems may be categorized as non-video based systems and video based systems. Since video based systems are non-contacting, they have the advantage of being less obtrusive and more comfortable to the user.

The direction of a person's gaze is determined by a combination of their face orientation and eye orientation. When the head is held fixed so that the 3-D positions of the eyeballs are known in a fixed reference frame, 3-D gaze tracking may be performed by eye tracking. A common technique for eye tracking employs a video camera for capturing images of the eye in which light, such as provided by infrared light emitting diodes, is reflected from the eye. The captured images of the eye are then analyzed to extract eye rotation from changes in reflections. Video based eye trackers typically use the corneal reflection (the first Purkinje image) and the center of the pupil as features to track over time. Alternatively, they may use reflections from the front of the cornea (first Purkinje image) and the back of the lens (fourth Purkinje image) as features to track.

When the user views a scene through a stereo viewer having left and right two-dimensional (2-D) display screens, gaze tracking becomes more complicated. Schematically, this situation is shown in FIG. 2. In this case, a projection of the point "P" is displayed as point "P1" on a left stereo image "I1" (being displayed in the left 2-D display screen) and another projection of the point "P" is displayed as point "P2" on the right stereo image "I2" (being displayed in the right 2-D display screen). The two points "P1" and "P2" are shown as being displaced horizontally in their respective images by a pixel disparity that maps to a depth which indicates the 3-D position of the point "P" on the object "O".

Thus, instead of both user eyes, "C1" and "C2", gazing at the same gaze point "P" such as schematically shown in FIG. 1, when viewing the scene in a stereo viewer, the left eye "C1" is gazing on a point "P1" on the left stereo image "I1" while the right eye "C2" is gazing on a point "P2" on the right stereo image "I2" such as schematically shown in FIG. 2. As a result, by merely tracking one of the eyes, it is not directly known where the other eye is gazing at the time on its 2-D display screen without a depth map for the scene being displayed. In this case, if the depth map for the scene is available (e.g., its 3-D surface contour), then a previously determined (e.g., at calibration) depth-to-disparity map may be used to convert the depth at the location of the tracked point on one 2-D display screen to the offset position (disparity) of its corresponding location in the other 2-D display screen.

One problem with relying on a depth map for the scene being displayed in the stereo viewer is the calculation of the depth map is computationally intensive and the scene may frequently change. Thus, it may not be practical to always have an updated depth map of the scene available.

Rather than tracking only one eye, the gazes of both eyes may be tracked on their respective 2-D display screens. The problem with this approach, however, is that two-eye tracking may be inherently unreliable due to one eye being dominant over the other or it may be prone to error as a result of the positioning of the lighting and/or the video camera relative to the eyes. Two eye tracking may also increase processing time and/or add components cost.

Since the conventional gaze tracking shown schematically in FIG. 1 is commonly referred to as 3-D gaze tracking because a 3-D position of the gaze point "P" is determinable as long as the positions and orientations of the eyes "C1" and "C2" are known, the situation shown schematically in FIG. 2 is referred to herein as stereo gaze tracking since it requires the determination of stereo gaze points "P1" and "P2" on the stereo viewer in order to estimate the 3-D position of the gaze point "P".

OBJECTS AND SUMMARY

Accordingly, one object of one or more aspects of the present invention is a method and system for stereo gaze tracking that does not require an updated depth map of the entire scene of a captured stereo image at all times.

Another object of one or more aspects of the present invention is a method and system for stereo gaze tracking that does not necessarily require both left and right eyes of a user to be tracked.

Another object of one or more aspects of the present invention is a method and system for stereo gaze tracking that improves the reliability of stereo gaze tracking performed by tracking both left and right eyes.

These and additional objects are accomplished by the various aspects of the present invention, wherein briefly stated, one aspect is a method for stereo gaze tracking, the method comprising: tracking a gaze point of a first eye of a user on a first one of right and left 2-D display screens; and estimating a gaze point of a second eye of the user on a second one of the right and left 2-D display screens by processing information of the tracked gaze point of the first eye and information of right and left stereo images of the scene respectively being displayed on the right and left 2-D display screens.

Another aspect is a system comprising: a stereoscopic camera for capturing right and left stereo images of a scene; a stereo viewer having right and left 2-D display screens disposed so as to align with right and left eyes of an user, wherein the right and left 2-D display screens respectively display information of right and left stereo images of the scene captured by a stereoscopic camera; a first tracking system configured to track a gaze point of a first eye of the user on a first one of the right and left 2-D display screens; and a processor configured to estimate a gaze point of a second eye of the user on a second one of the right and left 2-D display screens by processing information of the tracked gaze point of the first eye and the information of the right and left stereo images of the scene.

Additional objects, features and advantages of the various aspects of the present invention will become apparent from the following description which should be taken in conjunction with the accompanying drawings.

DETAILED DESCRIPTION

In a stereo vision system employing the present invention, a user views a 3-D scene in a stereo viewer, wherein the 3-D scene has been captured by a stereoscopic camera and the stereo viewer has left and right 2-D display screens spaced apart to be respectively viewable by the user's left and right eyes so as to provide a 3-D perception of the scene displayed therein.

There are many applications for such a stereo system. For example, it may be employed in a virtual reality system in which the stereo viewer is implemented in goggles worn by the user. In another example it may be employed in a minimally invasive robotic system such as marketed by Intuitive Surgical, Inc. of Sunnyvale, Calif.

Minimally Invasive Robotic System

Figure 1:
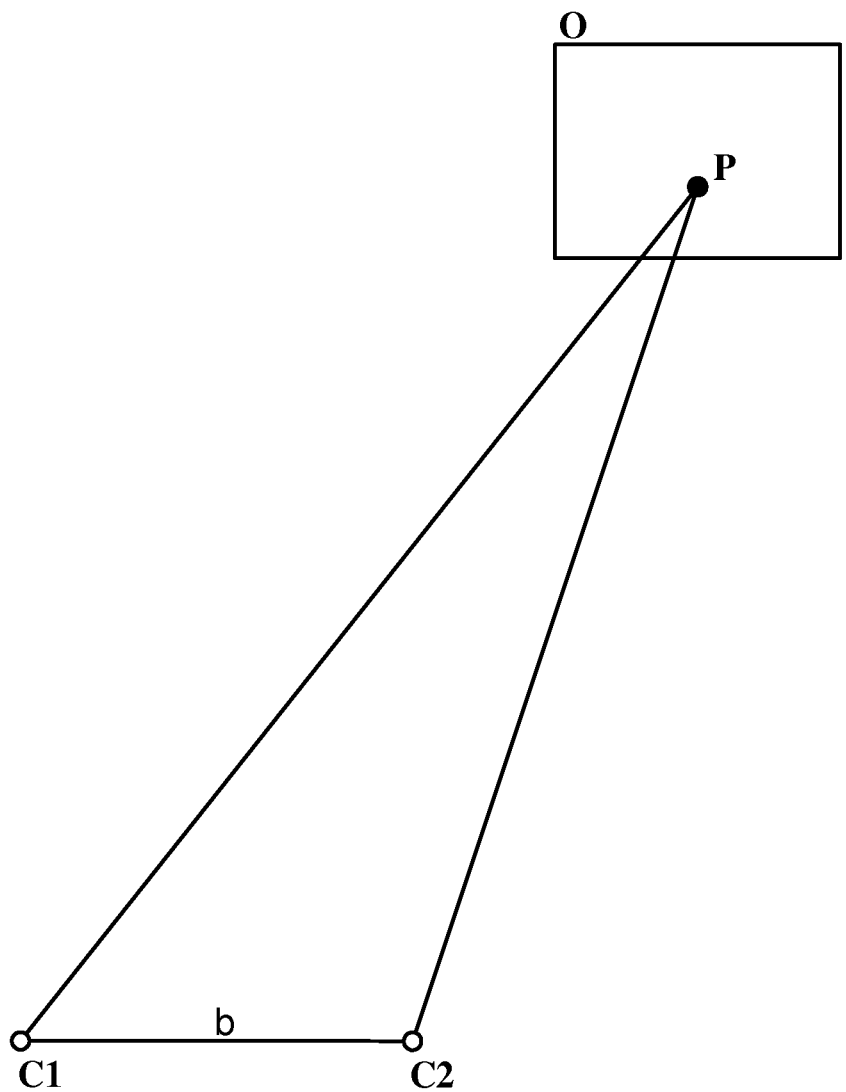
FIG. 1 schematically illustrates viewing of a 3-D gaze point.
Figure 2:
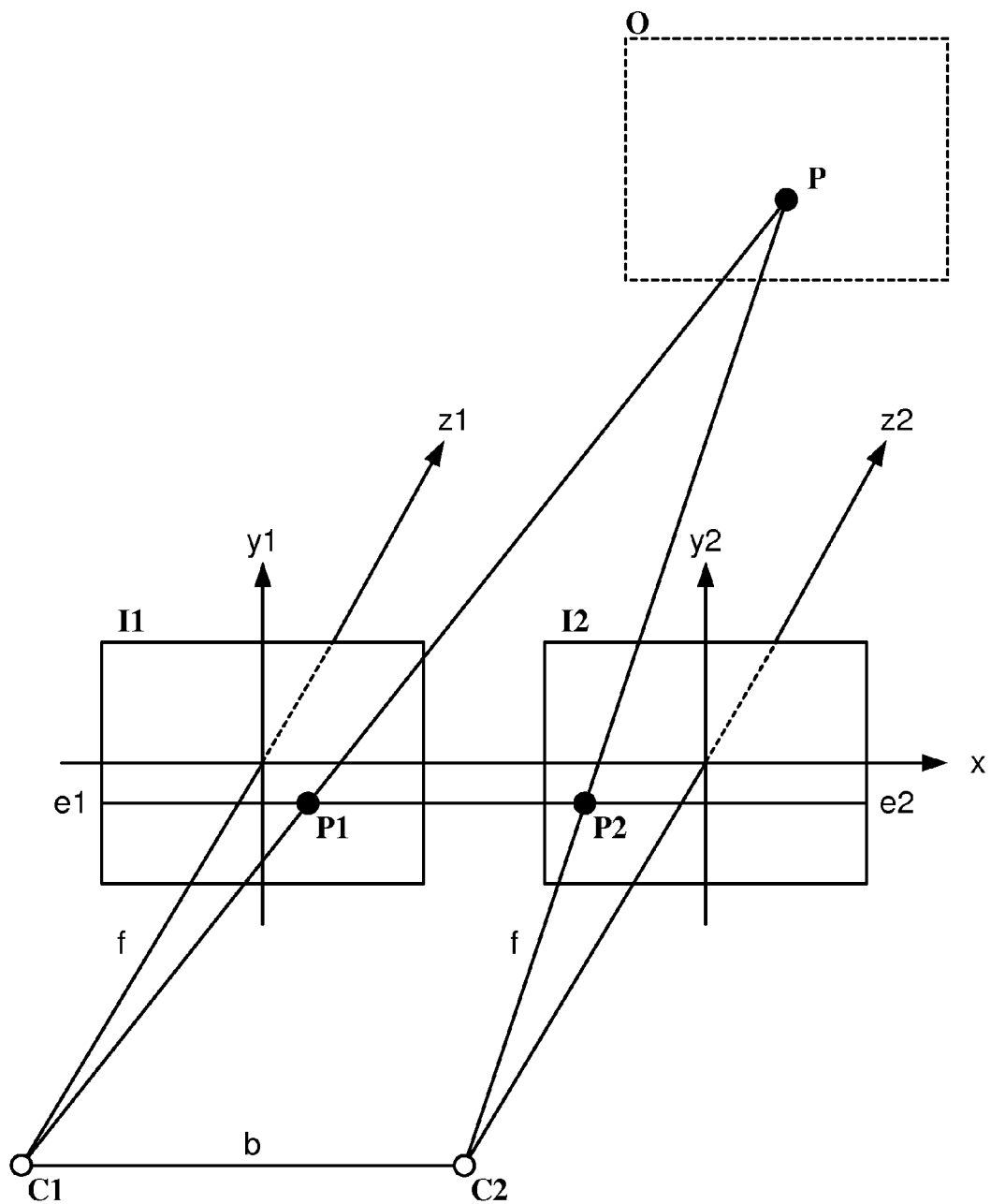
FIG. 2 schematically illustrates viewing of a 3-D gaze point by its projections on left and right stereo images.
Figure 3:
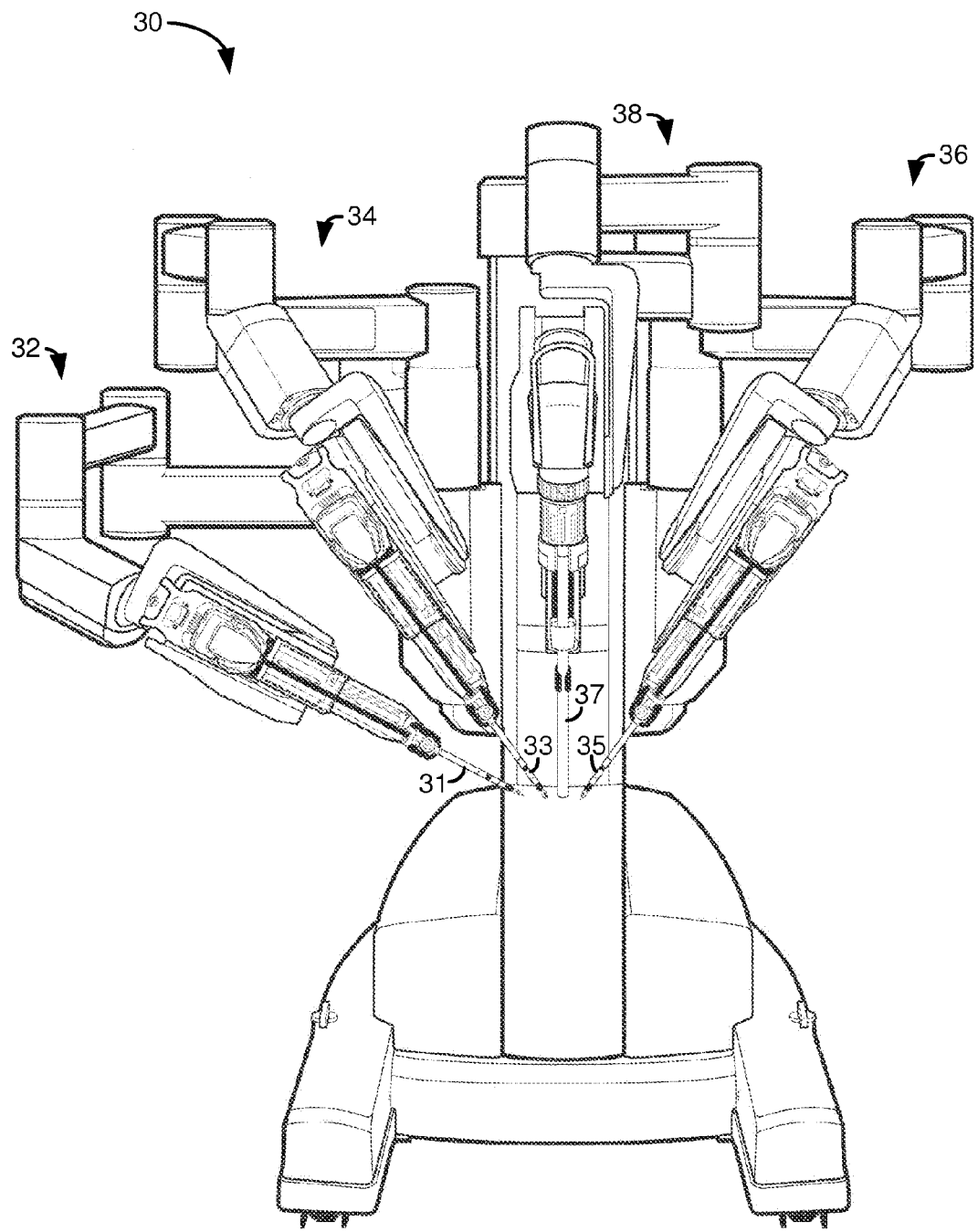
FIG. 3 illustrates a front view of a cart with multiple robotic arms.

FIG. 3 illustrates a work site cart 30 having robotic arms 32, 34, 36, 38 that hold and manipulate devices 31, 33, 35, 37. In this example, the devices 31, 33, 35 are tools or instruments that may be employed to perform a procedure on an object at a work site and the device 37 includes a stereoscopic camera for capturing stereo images of the work site while the procedure is being performed.

Figure 4:
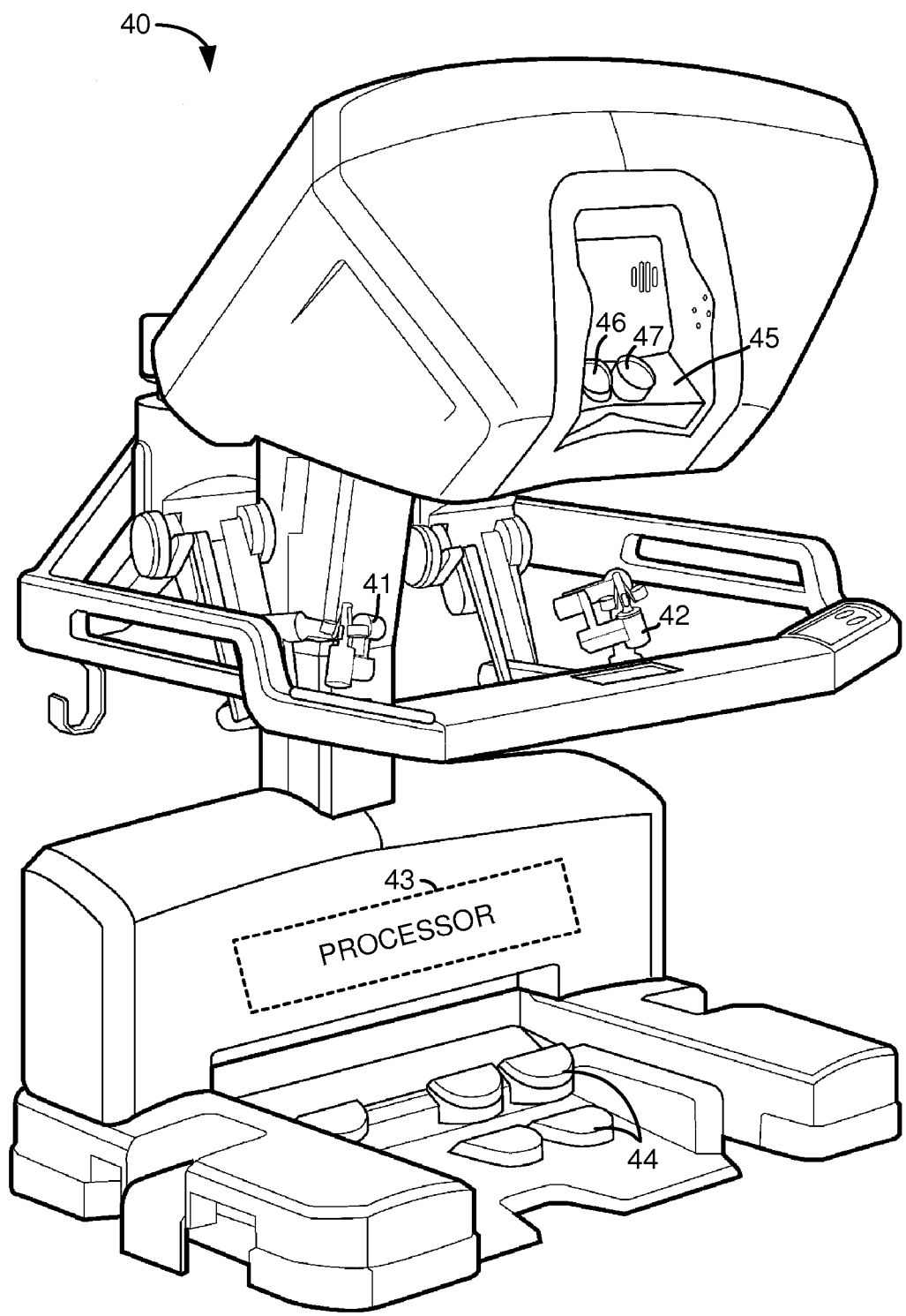
FIGS. 4 and 5 respectively illustrate perspective and front views of a master console with a stereo viewer.
Figure 5:
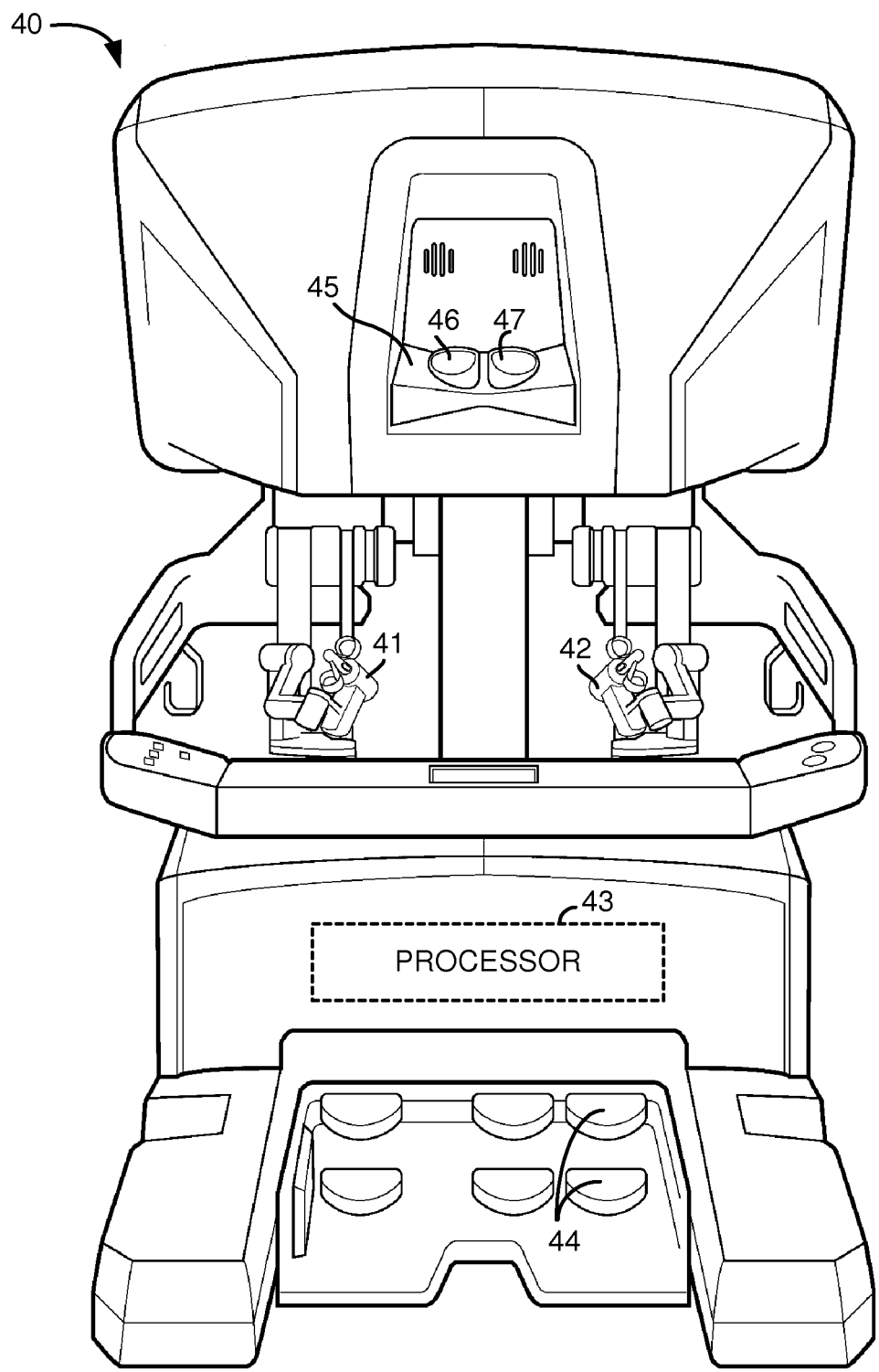

FIGS. 4 and 5 respectively illustrate perspective and front views of a master console 40 which a user operates for controlling the robotic arms 32, 34, 36, 38 and devices 31, 33, 35, 37 of the cart 30, which it communicates with locally or remotely over one or more communication lines. The master console 40 has left and right input devices 41, 42 which the user may grasp respectively with his/her left and right hands to manipulate associated devices such as devices 33, 35 of the cart 30 in preferably six degrees-of-freedom. Foot pedals 44 with toe and heel controls are also provided on the master console 40 so the user may control movement and/or actuation of other devices such as auxiliary device 31 and imaging device 37. A processor 43 is also provided in the master console 40 for control and other purposes. Although shown as a single processor 43 located in the base of the master console 40, the processor 43 may be implemented as multiple cooperative processors distributed in the master console 40 as well as other parts of the minimally invasive robotic system.

Additional details on a minimally invasive robotic system such as described herein may be found, for example, in U.S. 2010/0166323 A1 "Robust Sparse Image Matching for Robotic Surgery"; U.S. Pat. No. 6,493,608 B1 "Aspects of a Control System of a Minimally Invasive Surgical Apparatus"; and U.S. Pat. No. 7,155,315 B2 "Camera Referenced Control in a Minimally Invasive Surgical Apparatus"; each of which is incorporated herein by reference.

Stereo Vision System

A stereo viewer 45 is also provided in the master console 40 so that the user may view the work site in stereo vision from images captured by the stereoscopic camera of the imaging device 37. Left and right eyepieces, 46 and 47, are provided in the stereo viewer 45 so that the user may view left and right 2-D display screens inside the viewer 45 respectively with the user's left and right eyes. Conventional mechanisms are provided for both adjusting the distance between the left and right eyepieces, 46 and 47, to accommodate different pupillary distances of users and adjusting the distances of the left and right eyepieces, 46 and 47, to their respective left and right 2-D display screens for user focusing purposes.

Additional details on the stereo imaging aspects of the stereo vision system may be found, for example, in U.S. Pat. No. 6,720,988 B1 "Stereo Imaging System and Method for Use in Telerobotic Systems", which is incorporated herein by reference.

Since the user's left and right eye positions are known relative to the left and right 2-D display screens when the user places his/her eyes to the left and right eyepieces, 46 and 47, the user's gaze on a 3-D gaze point in the stereo view may be tracked by tracking the user's left and right eyes. To this end, components of one or more eye tracking systems are integrated into the stereo viewer 45. To ensure accuracy and reliability of the eye tracking systems, they are calibrated before use using any suitable calibration procedure.

Figure 6:
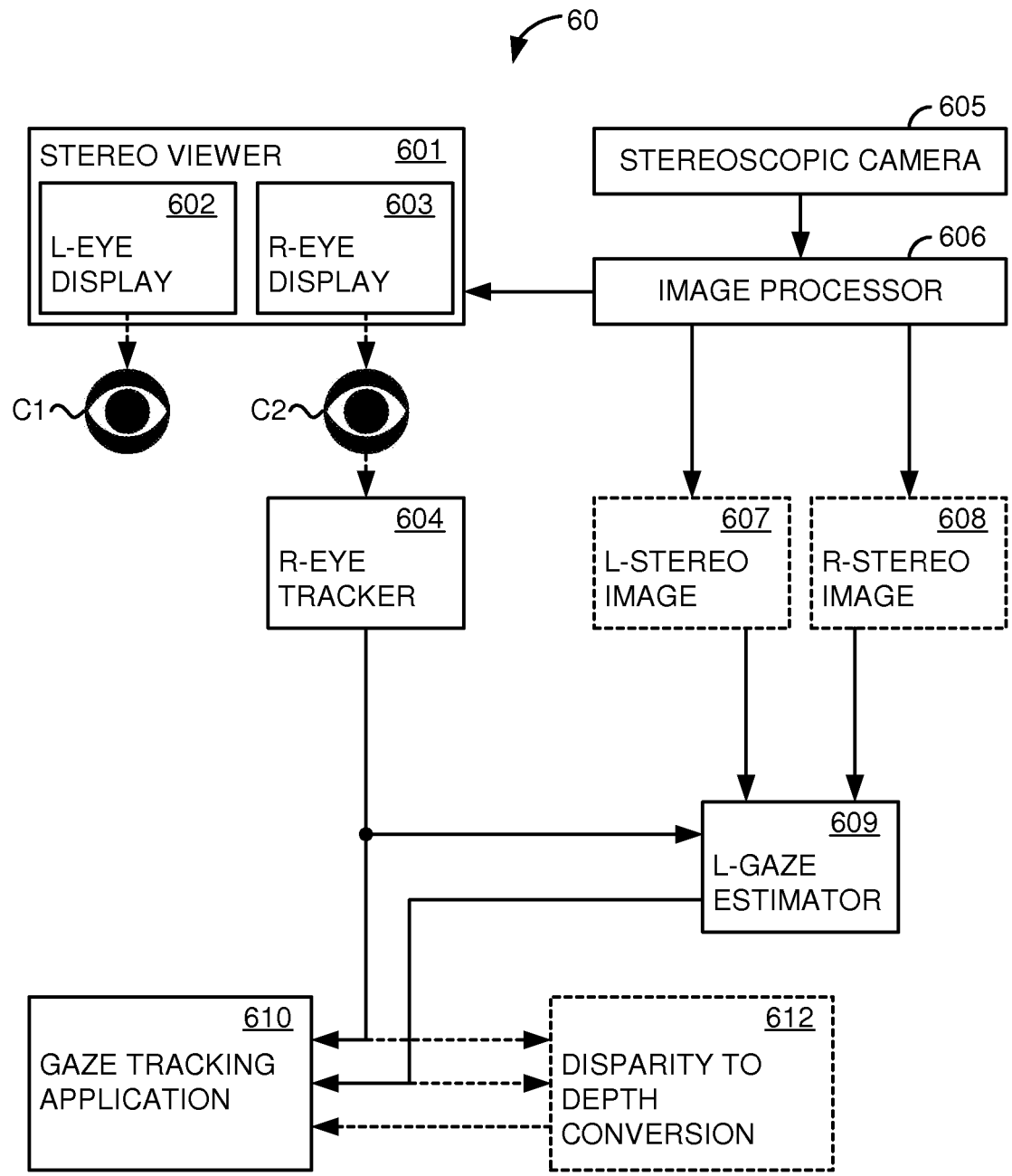
FIG. 6 illustrates a block diagram of a system for determining a 3-D gaze point of a user using a single eye tracker.

FIG. 6 illustrates a block diagram of a stereo vision system 60 with a single eye tracker. In this example, the single eye tracker is a right eye gaze point tracker 604 for tracking the gaze point of the right eye "C2" on the right 2-D display screen 603. In another example, the single eye tracker may be a left eye gaze point tracker for tracking the gaze point of the left eye "C1" on the left 2-D display screen 602. Since the stereo vision system 60 operates essentially the same whether a right or left eye tracker is used, albeit in a symmetrical fashion (e.g., switching nomenclature of right for left and vice versa in the description), only one—i.e., using the right eye gaze point tracker 604—is described herein.

The stereo vision system 60 also includes a stereoscopic camera 605 and stereo viewer 601 having the left and right 2-D display screens, 602 and 603, as previously discussed. An image processor 606 periodically processes raw video signals received from the stereoscopic camera 605 to generate pixilated left and right stereo images, 607 and 608, at each such process period, which are provided in proper format to the stereo viewer 601 for displaying the left stereo image 607 in the left 2-D display screen 602 and the right stereo image 608 in the right 2-D display screen 603. The user thereupon perceives the stereo images presented therein as a 3-D image of the work site when viewing the left and right 2-D display screens, 602 and 603, with his/her left and right eyes, "C1" and "C2" through the left and right eyepieces of the stereo viewer.

Although shown as a separate block 604 from the stereo viewer 601, parts of the right eye gaze point tracker 604 are included in the stereo viewer 601. In particular, the stereo viewer includes one or more light sources such as one or more infrared Light Emitting Diodes (IR LEDs) for directing light onto the right eye of the user, a reflected light or image capturing device such as a Charge Coupled Device (CCD) camera, and one or more mirrors such as Dichroic mirrors for directing the reflected light from and/or image of the right eye of the user to the reflected light or image capturing device. Information of the reflected light or captured image of the right eye is then transmitted from the reflected light or image capturing device to the processor 43 so that the information may be analyzed using known techniques to determine the gaze and gaze point of the user's right eye on the right 2-D display screen 603.

A left eye gaze point estimator 609 receives information of the tracked right eye gaze point from the right eye gaze point tracker 604 and information of the left and right stereo images, 607 and 608, from the image processor 606. It then processes the received information to generate an estimate for the left eye gaze point on the left 2-D display screen 602. As previously explained, if a depth map indicating the distance of each viewable surface point in the work site from the perspective of the stereoscopic camera has been determined, then it is a simple matter of referring to the depth map to determine the depth associated with the tracked gaze point of the right eye on the right 2-D display screen 603 and convert the depth to a disparity or pixel offset to estimate a corresponding gaze point of the left eye on the left 2-D display screen 602. Alternatively, a disparity map may be generated for corresponding points of the left and right 2-D display screens, 602 and 603, so that the disparity between the two pixel points may be determined directly. When such a depth or disparity map is unavailable, however, the estimation of the left eye gaze point on the left 2-D display screen 602 may be determined using image matching techniques such as a robust sparse image matching algorithm as described later herein.

A gaze tracking application 610 may then directly use the tracked right eye gaze point on the right display screen 603, which is received from the right eye gaze point tracker 604, and the estimated left eye gaze point on the left display screen 602, which is received from the left eye gaze point estimator 609, to perform one or more user selectable applications.

Alternatively, the gaze tracking application 610 may use a 3-D gaze point corresponding to the tracked right eye and estimated left eye gaze points to perform the one or more user selectable applications. If a depth map for the right eye display screen 603 is available so that the depth is known for the tracked right eye gaze point, then determination of the 3-D gaze point is straightforward. On the other hand, if a depth map is not available, then a disparity to depth conversion block 612 may be provided to generate the 3-D gaze point from the tracked right eye gaze point on the right 2-D display screen 603, which is provided by the right eye gaze point tracker 604, and the estimated left eye gaze point on the left 2-D display screen 602, which is provided by the left eye gaze point estimator 609. For example, such a conversion may be performed by measuring the pixel offset for the tracked and estimated gaze points respectively on the right and left 2-D display screens, 603 and 602, and applying the disparity to a disparity-to-depth map generated, for example, during calibration of the stereoscopic camera 605.

Figure 7:
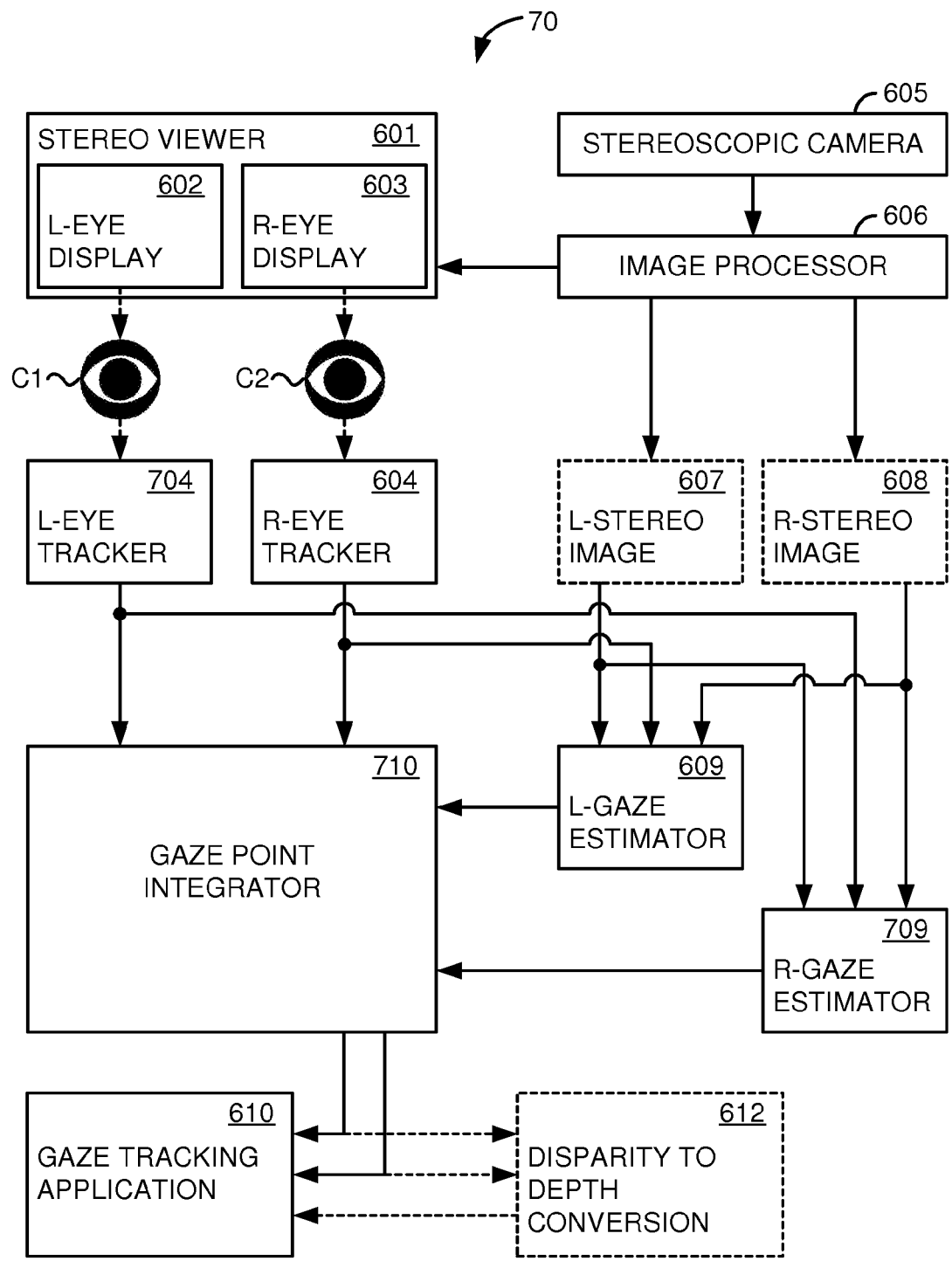
FIG. 7 illustrates a block diagram of a system for determining a 3-D gaze point of a user using dual eye trackers.

FIG. 7 illustrates another stereo vision system 70 with dual eye trackers—a left eye gaze point tracker 704 for tracking a gaze point of the left eye on the left 2-D display screen 602 and the right eye gaze point tracker 604 for tracking the gaze point of the right eye on the right 2-D display screen 603. As previously explained, although the 3-D gaze point may be obtained by tracking both the left and right eyes respectively on the left and right 2-D display screens, 602 and 603, errors may occur due to either the right or left eye being the dominant eye. Errors may also occur due to the position of the one or more light source relative to the left and right eyes or the position of the reflected light or image capturing device relative to the left and right eyes (e.g., shadows, obstructions, poor reflection angles, etc., affecting the accuracy of tracking one eye more than the other).

Also included in the stereo vision system 70 are a gaze point integrator 710, the left eye gaze point estimator 609, and a right eye gaze point estimator 709 to compensate for such previously described errors and therefore improve the reliability and/or accuracy of the determination of the 3-D gaze point. The left eye gaze point estimator 609 generates an estimation of the left eye gaze point on the left 2-D display screen 602 using the tracked right eye gaze point from the right eye gaze point tracker 604 and the left and right stereo images, 607 and 608, from the image processor 606, as previously described. In a similar, but symmetrical manner, the right eye gaze point estimator 709 generates an estimation of the right eye gaze point on the right 2-D display screen 603 using the tracked left eye gaze point from the left eye gaze point tracker 704 and the left and right stereo images, 607 and 608, from the image processor 606.

Confidence scores for the left and right eye trackers, 704 and 604, may be determined so that improved determinations of the left and right eye gaze points may be made by the gaze point integrator 710 according to the confidence scores. For example, the determinations of the left and right eye gaze points may be improved on by adjusting the tracked left and right eye gaze points according to their respective confidence scores and estimated left and right eye gaze points as follows:

$$GP_R = C_{RT} \cdot GP_{RT} + (1 - C_{RT}) \cdot GP_{RE}$$

$$GP_L = C_{LT} \cdot GP_{LT} + (1 - C_{LT}) \cdot GP_{LE}$$

where "$GP_R$" and "$GP_L$" are the determinations made by the gaze point integrator 710 for the right and left eye gaze points, "$C_{RT}$" and "$C_{LT}$" are the right and left tracking confidence scores (where "1" is the highest and "0" is the lowest), "$GP_{RT}$" and "$GP_{LT}$" are the tracked right and left eye gaze points, and "$GP_{RE}$" and "$GP_{LE}$" are the estimated right and left eye gaze points.

Thus, when the confidence score for tracking one of the eyes is high, the gaze point integrator 710 will more heavily weigh the output of the eye tracker relative to that of the gaze point estimator in making its determination of the gaze point for that eye. Conversely, when the confidence score for tracking one of the eyes is low, the gaze point integrator 710 will more heavily weigh the output of the gaze point estimator relative to that of the eye tracker in making its determination of the gaze point for that eye.

The tracking confidence scores, "$C_{RT}$" and "$C_{LT}$", may be determined directly by their respective right and left eye gaze point trackers, 604 and 704, based on image quality and other criteria, and may be refined by the gaze point integrator 710 using temporal trajectories of the tracked right and left gaze points. As an example, a confidence score received from a gaze point tracker may be lowered when the tracked gaze point results in an abrupt change from immediately prior-in-time tracked gaze points by the gaze point tracker.

Confidence scores for the left and right eye gaze point estimators, 609 and 709, may also be determined so that improved determinations of the left and right eye gaze points may be made by the gaze point integrator 710 according to the confidence scores. Since estimation of the left eye gaze point uses the tracked right eye gaze point and image matching of the left and right stereo images, the confidence score for the estimated left eye gaze point is a function of both the confidence score of the right eye gaze point tracking and a confidence score for the image matching. Likewise, since estimation of the right eye gaze point uses the tracked left eye gaze point and image matching of the right and left stereo images, the confidence score for the estimated right eye gaze point is a function of both the confidence score of the left eye gaze point tracking and a confidence score for the image matching.

With the availability of these additional confidence scores, the gaze point integrator 710 may further refine its determinations of the left and right eye gaze points. For example, the determination of the left and right eye gaze points may be improved on by adjusting the tracked left and right eye gaze points according to weighted averages of the tracked and estimated confidence scores as follows:

$$GP_R = \frac{C_{RT}}{C_{RT} + C_{RE}} \cdot GP_{RT} + \frac{C_{RE}}{C_{RT} + C_{RE}} \cdot GP_{RE}$$

$$GP_L = \frac{C_{LT}}{C_{LT} + C_{LE}} \cdot GP_{LT} + \frac{C_{LE}}{C_{LT} + C_{LE}} \cdot GP_{LE}$$

where "$GP_R$" and "$GP_L$" are the determinations made by the gaze point integrator 710 for the right and left eye gaze points, "$C_{RT}$" and "$C_{LT}$" are the right and left tracking confidence scores, "$C_{RE}$" and "$C_{LE}$" are the right and left estimation confidence scores, "$GP_{RT}$" and "$GP_{LT}$" are the tracked right and left eye gaze points, and "$GP_{RE}$" and "$GP_{LE}$" are the estimated right and left eye gaze points.

The estimation confidence scores, "$C_{RE}$" and "$C_{LE}$", may be determined directly as a function (e.g., a product) of the tracked and image matching confidence scores. The confidence scores may then be refined in a similar manner as the tracked confidence scores. For example, the right confidence score may be determined by the deviation between the current output of the right eye gaze point estimator 709 and prior-in-time outputs of the right eye gaze point estimator 709, wherein a relatively small deviation results in a relatively high confidence score and a relatively large deviation results in a relatively low confidence score. In a similar manner, the left confidence score may be determined by the deviation between the current output of the left eye gaze point estimator 609 and prior-in-time outputs of the left eye gaze point estimator 609.

In addition to adjusting the tracked left and right gaze points using weighted averages of the tracked and estimated gaze points and confidence scores as previously described, the gaze point integrator 710 may further improve its determination of the left and right gaze points, $GP_L$ and $GP_R$, which it provides to the gaze tracking application 610, by using information of the trajectories of the tracked and estimated left and right gaze points. For example, the shape of the temporal trajectory for a gaze point trajectory having a high confidence score may be used to estimate the temporal trajectory for a gaze point trajectory having a low confidence score.

The left and right eye gaze points determined by the gaze point integrator 710 may then be processed through the gaze tracking application 610 as previously described in reference to FIG. 6. Although shown as separate blocks 604, 704, 609, 709, 710, 606, 610, and 612, the processing performed in these blocks may all be performed by the processor 43 of the master console 40. Alternatively, the processing of one or more of these blocks, such as the image processor 606, may be performed by a separate processor or circuitry dedicated to performing specific tasks.

Robust Sparse Image Matching Algorithm

One technique implementable in the left and right eye gaze point estimators, 609 and 709, for estimating the left and right eye gaze points respectively on the left and right 2-D display screens, 602 and 603, is robust sparse image matching, such as described, for example, in the previously incorporated by reference U.S. 2010/0166323 A1 "Robust Sparse Image Matching for Robotic Surgery". At least three matching methods can be selectively combined to perform robust sparse image matching: (i) coarse-to-fine global offset, (ii) coarse-to-fine region matching based on normalized cross correlation, and (iii) point matching based on feature detection and matching. The locations of points with an extremely low matching score can be inferred from matched locations of other good points. In addition, other constraints, such as soft epi-polar constraints, for example without camera calibration, can be added with the first step of global offset estimation. The locations of points of interest with extremely low confidence scores can be interpolated from the locations of other points of interest that have been matched with good confidence scores.

Figure 8:
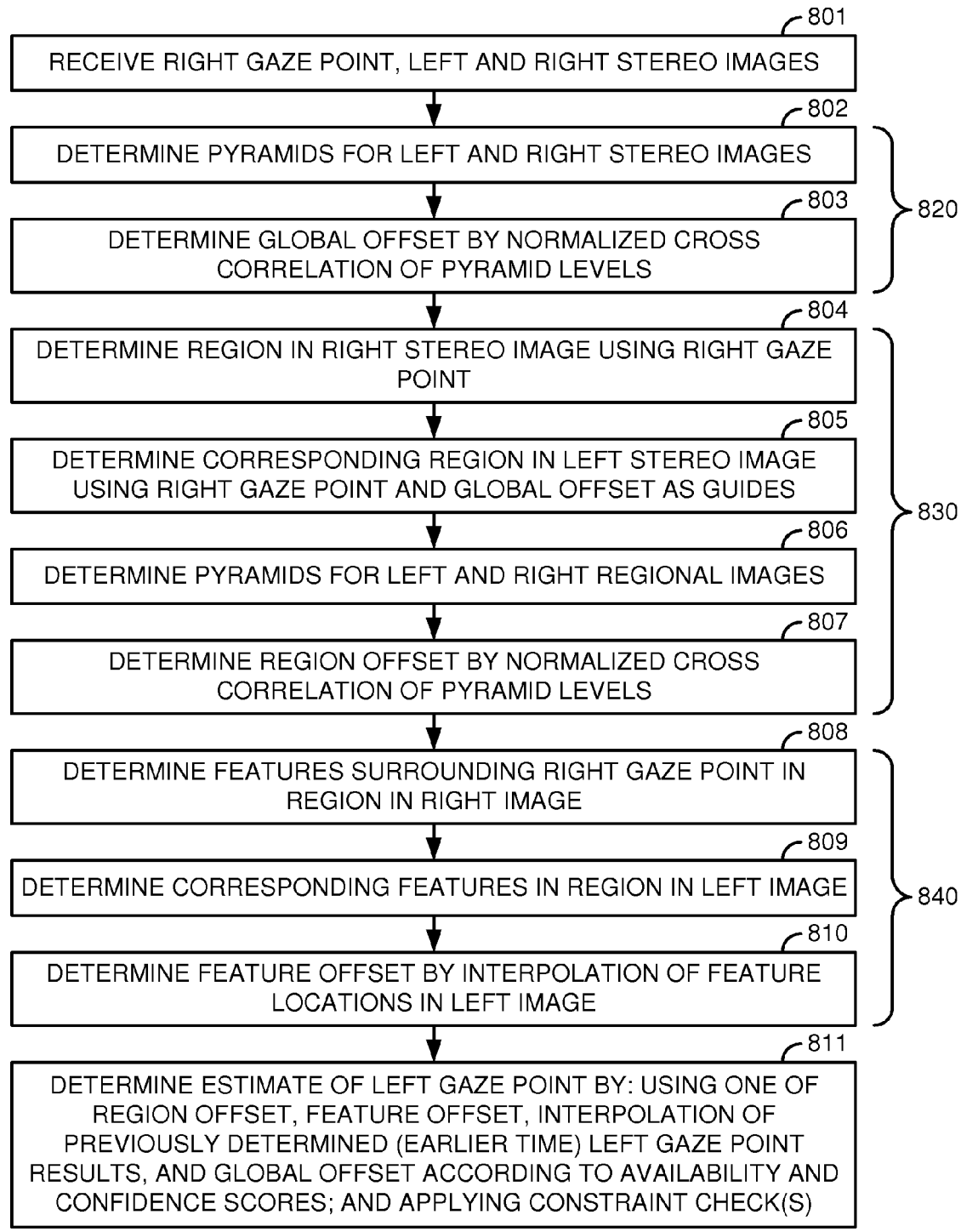
FIG. 8 illustrates a flow diagram of a method for estimating a gaze point of a user on a 2-D display screen of a stereo viewer.

FIG. 8 illustrates an example of one method executed by the left eye gaze point estimator 609 for performing the estimation of the left eye gaze point on the left 2-D display screen 602. A symmetrical method may be used for estimation of the right eye gaze point on the right 2-D display screen 603 by the right eye gaze point estimator 709. Although the method describes the performance of three matching methods: (i) coarse-to-fine global matching 820 to determine a global offset, (ii) coarse-to-fine region matching 830 to determine a region offset, and (iii) feature matching 840 to determine a feature offset, it is to be appreciated as explained above that these and other methods can be selectively combined to perform robust sparse image matching. Further, although examples are described for performing these matching methods, it is to be appreciated that the invention is not to be unnecessarily limited by the examples described herein and is to include in its scope all other known, now and in the future, techniques for performing these and other matching methods to be used by the left and right eye gaze point estimators, 609 and 709.

In block 801, the method receives information of the tracked right eye gaze point from the right eye tracker 604 and information of the left and right stereo images, 607 and 608, from the image processor 606. Although activities performed for the current process period is only described, it is to be appreciated that the method periodically receives the outputs of the right eye tracker 604 and image processor 606 so periodic estimates of the left eye gaze point on the left 2-D display screen 602 may be determined for corresponding time periods.

A coarse-to-fine global matching 820 of the left and right stereo images, 607 and 608, may be performed in blocks 802-803 to determine a global offset of the left and right stereo images. The global offset may be used as a coarse estimate for determining the pixel offset between the right and left eye gaze points on the right and left stereo images, 608 and 607, being displayed at the time respectively in the right and left 2-D display screens, 603 and 602. The coarsely determined pixel offset estimate may then be used to determine a coarse estimate for the left eye gaze point in the left 2-D display screen 602.

In block 802, global matching determines a Laplacian (or other suitable type of) pyramid for each of the left and right stereo images. As an example, for each of the left and right stereo images, 607 and 608, Gaussian blurring may be performed to blur the image, decimation may be performed on the blurred image to reduce the size of the image, expansion may be performed on the decimated image to expand the image, and subtraction of the original image from the processed image may be performed to obtain the Level "0" image of the pyramid. Subsequent levels of the pyramid may be constructed until Level "n" of the pyramid is constructed. In block 803, global matching determines a global offset of the left and right stereo images, 607 and 608, by normalized cross correlation of corresponding levels of the left and right pyramids generated in block 802.

A coarse-to-fine region matching 830 for determined regions of the left and right stereo images, 607 and 608, may be performed in blocks 804-806 to determine a region offset of corresponding regions in the left and right stereo images. The region offset may be used as an intermediate level estimate for determining the pixel offset between the right and left eye gaze points on the right and left stereo images, 608 and 607, being displayed at the time respectively in the right and left 2-D display screens, 603 and 602, and consequently, an intermediate level estimate for the left eye gaze point in the left 2-D display screen 602.

In block 804, region matching determines a region about the right eye gaze point in the right stereo image 608, which is being displayed at the time in the right 2-D display screen 603, for matching in the left stereo image 607, which is being displayed at the time in the left 2-D display screen 602. The global offset determined by global matching 820 may be used as a guide in determining the size of the region about the right eye gaze point. In block 805, region matching determines the location of a corresponding region in the left stereo image 607 using the right eye gaze point and the global offset as guides to define an area in the left stereo image 607 in which the left eye gaze point is likely to be found. As with the global offset 820, the region matching may be performed in a coarse-to-fine manner. In block 806, the region matching determines Laplacian (or other suitable types of) pyramids for each of the right and left stereo image regions, in a similar manner as described in reference to block 802. In block 807, region matching determines a region offset of the left and right stereo image regions by (i) normalized cross correlation of corresponding levels of the left and right pyramids generated in block 806 to generate corresponding correlation surfaces, (ii) determining the optimal level for region matching using statistical analysis, and (iii) determining the region offset by determining a maximum value of the correlation surface of the optimal level of the pyramid.

Feature matching 840 in the regions used for region matching may be performed in blocks 808-810 to determine a feature offset that indicates the pixel offset between the right eye gaze point on the right 2-D display screen 603 and the left eye gaze point on the left 2-D display screen 602. Compared to the global and region offsets, the feature or gaze point offset indicates the finer estimate for the left eye gaze point in the left 2-D display screen 602.

In block 808, feature matching determines features in the region used for region matching of the right 2-D display screen 603 based upon how easily they are identifiable and their positions relative to the right eye gaze point on the right 2-D display screen 603. For example, pixels with high intensity gradients relative to their neighboring pixels that are also distributed about the right eye gaze point may be suitable candidates for such features. In block 809, feature matching determines or identifies the corresponding features in the left 2-D display screen 602. The features of the right stereo image 608 being displayed at the time in the 2-D display screen 603 can be matched with corresponding features in the left stereo image 607 being displayed at the time in the 2-D display screen 602 in many ways. For example, the features of the right stereo image 608 can be matched to the left stereo image 607 with at least one of Harris corner detection, scale-space extrema detection, local extreme detection, or scale invariant transform. A known scale invariant feature transform is described in "Distinctive Image Features from Scale-Invariant Keypoints", authored by David Lowe and published in the International Journal of Computer Vision, 2004 (the "Lowe publication"). In block 810, the known spatial relationship between the right eye gaze point and the features in the right stereo image 608 (that were determined in block 808) is used to estimate the location of the left eye gaze point by interpolation of the matched features in the left stereo image 607 (that were determined in block 809). The feature offset is then simply the pixel offset between the right and left eye gaze points respectively in the right and left stereo images, 608 and 607.

In block 811, matching integration is performed to determine the estimate of the left eye gaze point on the left 2-D display screen 602 (which is displaying at the time the left stereo image 607) by using one of the region offset determined from the coarse-to-fine region matching 830, the feature offset determined from the feature matching 840, interpolation of previously determined (earlier in time) left eye gaze point estimation results, and the global offset determined in the coarse-to-fine global offset 820, according to availability and confidence scores.

In any or all of global matching 820, region matching 830, feature matching 840, and matching integration 811, constraint checks may be applied to determine the validity of results and/or used to simplify a matching process by limiting the search window based upon the constraint and/or by searching for an additional value when the matched point comprises a location outside the constraint. Examples of such constraint checks include a soft epi-polar constraint, a focus constraint, and a depth constraint.

Figure 9:
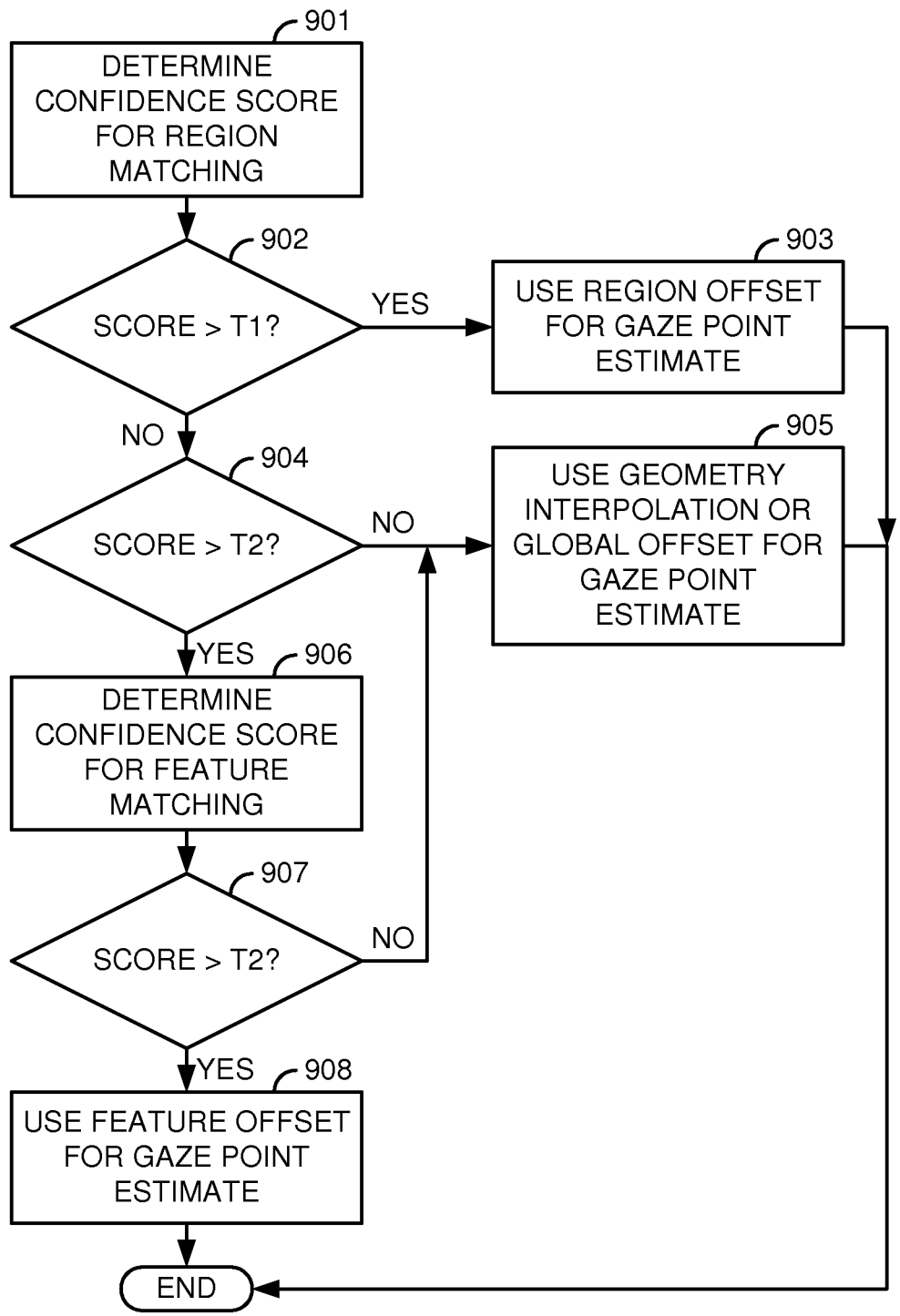
FIGS. 9, 10 and 11 illustrate flow diagrams of examples for performing the matching integration as performed in the method of FIG. 8.
Figure 10:
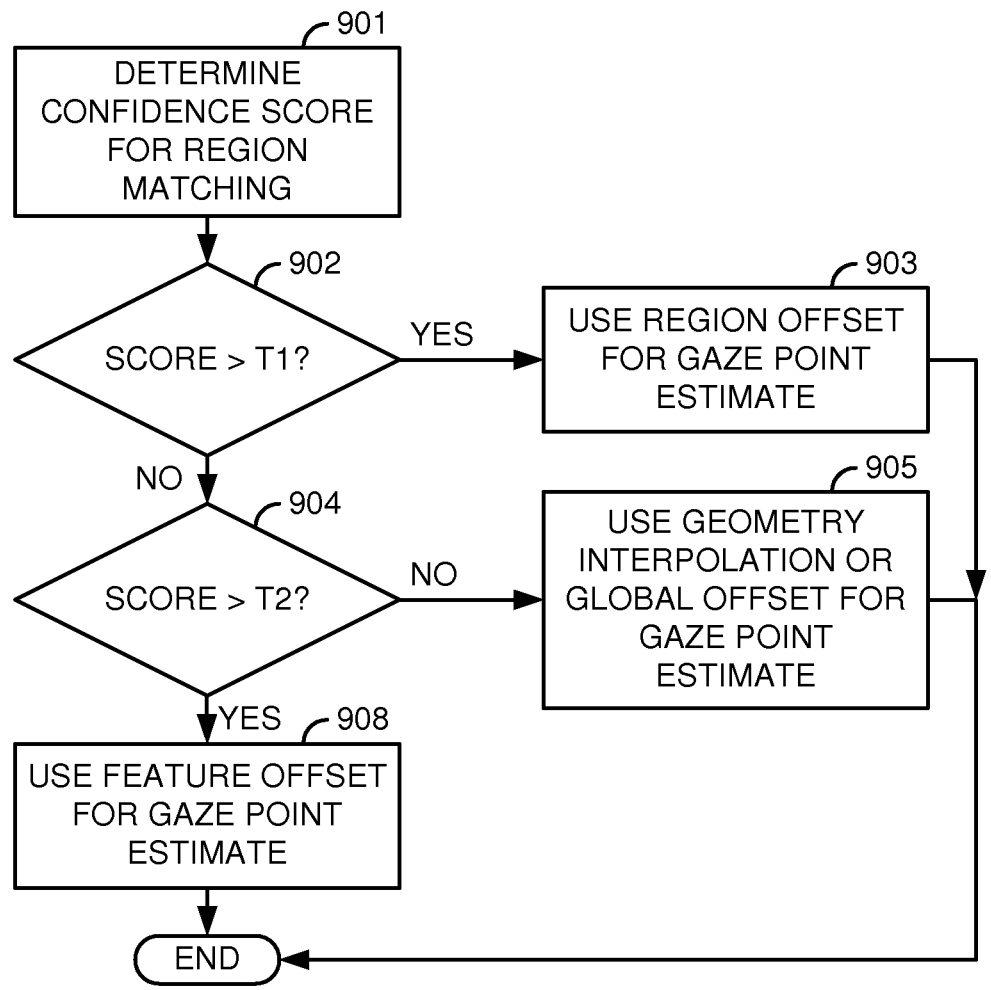
Figure 11:
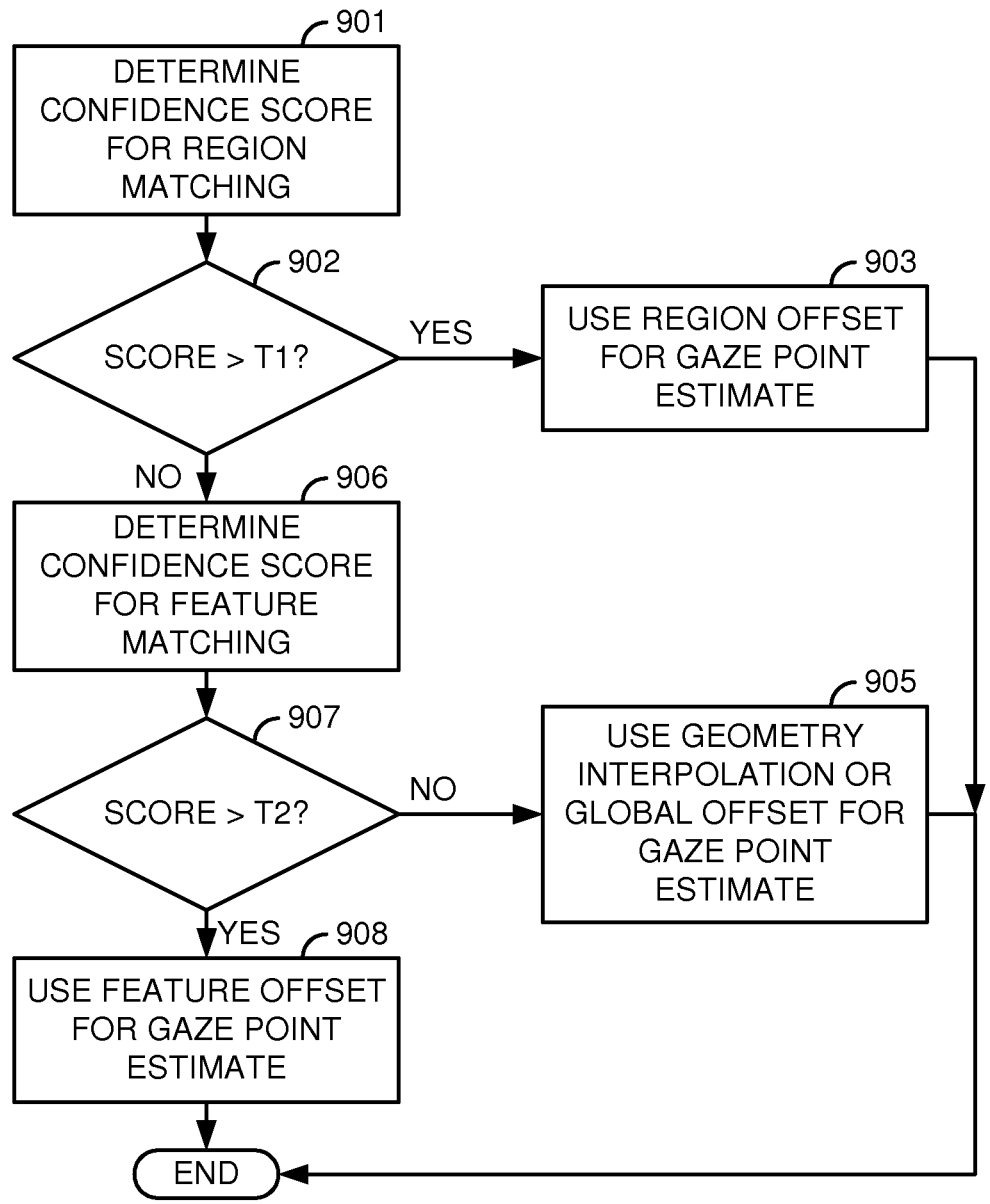

FIGS. 9-11 illustrate various examples of methods for performing the matching integration block 811 of FIG. 8. In the figures that follow, blocks with the same reference number indicate blocks in which identical processing is performed.

FIG. 9 illustrates a first example of a method for performing the matching integration block 811 of FIG. 8.

In block 901, a confidence score for the region matching performed in blocks 830 is either determined or a confidence score previously determined during the region matching is retrieved. The confidence score for region matching may be determined in many ways. The confidence score may comprise known measures of the quality with which the region of the right 2-D display screen 603 (which is displaying the right stereo image 608 at the time) is matched to the left stereo image 607. For example, the confidence score may comprise at least one measure of goodness of fit, such as an $R^2$ value based on local linear regression of one-way matching results, i.e., pixel offsets from neighboring points. The confidence score may also be obtained through two-way matching. That is, given the tracked gaze point "$GP_{RT}$", in the right stereo image 608, one can first find the matched point "$GP_{LE}$" on the left stereo image 607. One can then find for "$GP_{LE}$", the matched point "$GP_{RE}$" in the right stereo image 608. The confidence score is based on the distance between points "$GP_{RT}$" and "$GP_{RE}$". When cross correlation is used for matching, one can determine the confidence score based on a Gaussian fit of the correlation surface. In general, a sharper Gaussian surface suggests a higher confidence score. In many instances when the surface is not smooth and contains multiple local maxima, one may first find these local maxima corresponding to the matched point of interest and then fit them to a Gaussian function.

In block 902, the method determines whether the confidence score for region matching is greater than a first threshold value. If the determination in block 902 is YES, then in block 903, the region offset determined in or determinable from the region matching is determined to be used in block 811 of FIG. 8. The method then ends for the current process period.

On the other hand, if the determination in block 902 is NO, then in block 904, the method determines whether the confidence score for region matching is greater than a second threshold value, wherein the second threshold value is less than the first threshold value. If the determination in block 904 is YES, then in block 906, a confidence score for the feature matching performed in blocks 840 is either determined or a confidence score previously determined during the feature matching is retrieved. The confidence score may comprise known confidence measures for feature matching such as a probability density function, a ratio of a distance from a closest neighbor to a distance of a second closest neighbor, or a best bin first search. One example of determining a confidence score is described in the Lowe publication identified above.

In block 907, the method then determines whether the confidence score for feature matching is greater than the second threshold value. If the determination in 907 is YES, then in block 908, the feature offset determined in or determinable from the feature matching is determined to be used in block 811 of FIG. 8. The method then ends for the current process period.

On the other hand, if the determination in either block 904 or 907 is NO, then in block 905, the method checks the availability of previously determined (earlier in time) left eye gaze point estimation results. Typically, such results are stored in a memory accessible by the processor 43 (which implements the methods described herein). If no previously determined left eye gaze point estimates are available, then the method proceeds to use the global offset for its estimation of the left eye gaze point on the left 2-D display screen 602, and the method ends at this point for the current process period. On the other hand, if previously determined left eye gaze point estimates are available which are sufficiently close in time to suggest a fixation by the user's eyes on a gaze point and have acceptable confidence scores or other indicia of reliability, then conventional statistical techniques may be used to estimate the left eye gaze point on the left 2-D display screen 602 such as determining, for example, a centroid of the previously determined left eye gaze point estimates. Upon completion, the method ends for the current process period.

FIG. 10 illustrates a second example of a method for performing the matching integration block 811 of FIG. 8. This method is a modification of that described in reference to FIG. 9 with the exception that blocks 906 and 907 have been deleted. Thus, if the determination in block 904 is NO, the method uses the feature offset for the left eye gaze point estimate regardless of its confidence score.

FIG. 11 illustrates a third example of a method for performing the matching integration block 811 of FIG. 8. This method is another modification of that described in reference to FIG. 9 with the exception that block 904 has been deleted. Thus, the confidence score for region matching is only checked against the first threshold value, not the second threshold value.

Figure 12:
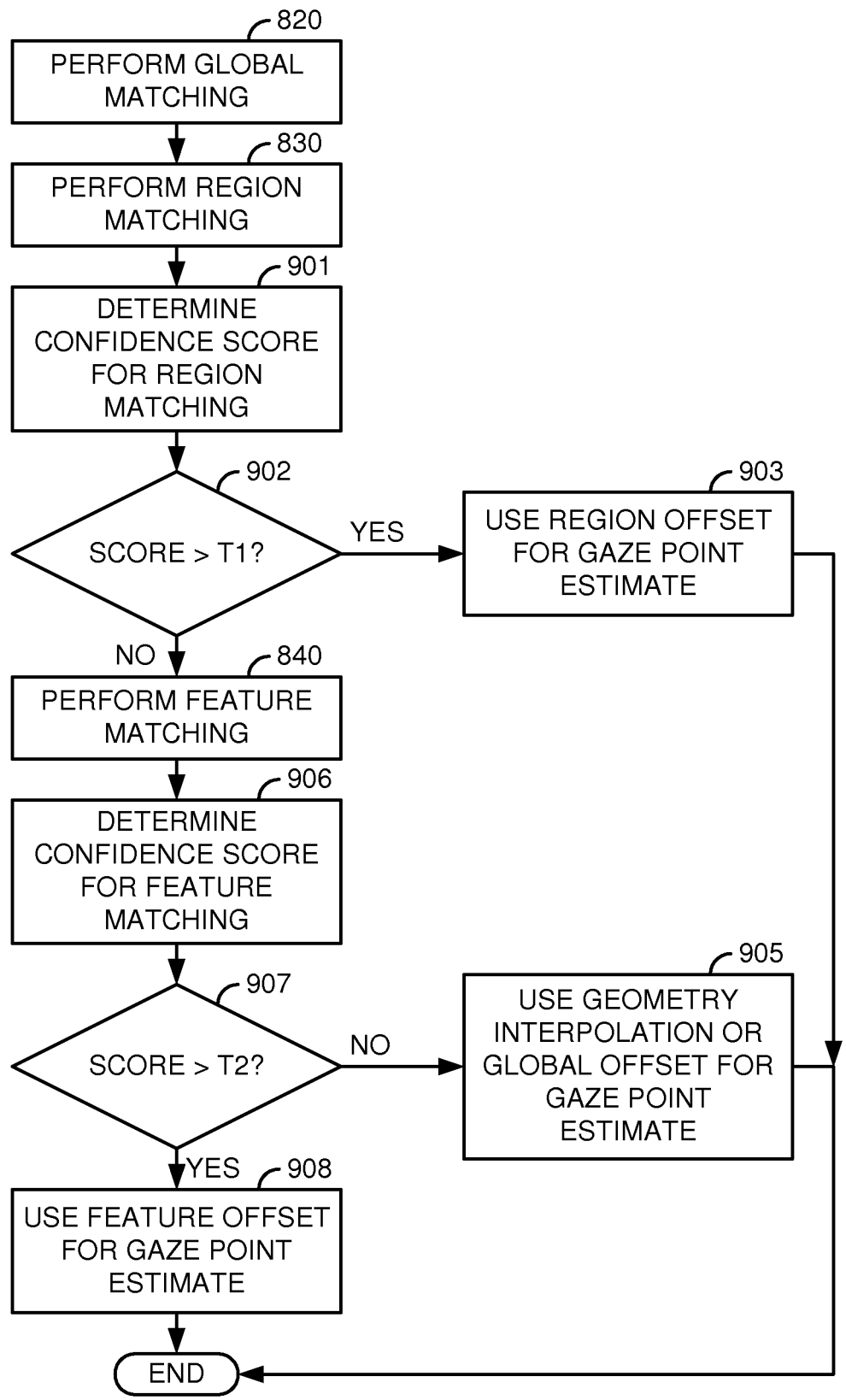
FIG. 12 illustrates a flow diagram of an alternative method for estimating a gaze point of a user on a 2-D display screen of a stereo viewer.

FIG. 12 illustrates an example of an alternative method executed by the left eye gaze point estimator 609 for performing the estimation of the left eye gaze point on the left 2-D display screen 602. As with the method described in reference to FIG. 8, a symmetrical method may be used for estimation of the right eye gaze point on the right 2-D display screen 603 by the right eye gaze point estimator 709. The method of FIG. 12 combines certain aspects of the method of FIG. 8 with the matching integration 811 as described in reference to FIG. 12 to reduce processing activities. In particular, in the method of FIG. 12, feature matching 840 is only performed if the confidence score for region matching 830 is less than the first threshold.

As may be appreciated, many other combinations and alterations to the methods described herein may be readily seen by those of skill in the art, and as such, are envisioned to be within the full scope of the present invention.

Although the various aspects of the present invention have been described with respect to one or more embodiments, it will be understood that the invention is entitled to full protection within the full scope of the appended claims.

What is claimed is:

1. A method for stereo gaze tracking, the method comprising:
    tracking, with a tracking system having a single-eye tracker, a gaze point of a first eye of a user on a first one of right and left two-dimensional display screens of a stereo viewer, wherein the right and left two-dimensional display screens respectively display information of right and left stereo images of a scene captured by a stereoscopic camera, wherein the right and left two-dimensional display screens are visible to the user through right and left eyepieces, respectively; and
    estimating, by a processor, a gaze point of a second eye of the user on a second one of the right and left two-dimensional display screens by processing information, received from the tracking system, describing the tracked gaze point of the first eye only and information of the right and left stereo images of the scene.

2. The method of claim 1, further comprising:
    estimating a three-dimensional gaze point using the tracked gaze point of the first eye and the estimated gaze point of the second eye of the user.

3. A method for stereo gaze tracking of a user, the method comprising:
    tracking, with a tracking system, a gaze point of a first eye of the user on a first one of right and left two-dimensional display screens of a stereo viewer, wherein the right and left two-dimensional display screens respectively display information of right and left stereo images of a scene captured by a stereoscopic camera;
    estimating, by a processor, a gaze point of a second eye of a user on a second one of the right and left two-dimensional display screens by processing information of the tracked gaze point of the first eye only and information of the right and left stereo images of the scene, wherein the processing of the information of the tracked gaze point of the first eye and the information of the right and left stereo images of the scene comprises:
  determining one or more of a global offset of the right and left stereo images, a region offset of corresponding regions of the right and left stereo images using the global offset and the tracked gaze point of the first eye, or a feature offset of corresponding features within the corresponding regions of the right and left stereo images; and
  estimating the gaze point of the second eye of the user on the second one of the right and left two-dimensional display screens by using one of the region offset, the feature offset, an interpolation of previously determined and prior-in-time gaze points of the second eye of the user, or the global offset according to a reliability of at least one of the determinations and an availability of the previously determined and prior-in-time gaze points of the second eye of the user.

4. The method of claim 3, wherein the determining of the global offset of the right and left stereo images comprises:
  determining a left pyramid for the left stereo image;
  determining a right pyramid for the right stereo image; and
  determining the global offset using a multi-level process based on normalized cross correlations of corresponding levels of the left and right pyramids.

5. The method of claim 3, wherein the determining of the region offset of corresponding regions of the right and left stereo images comprises:
  determining a region in the first one of the right and left two-dimensional display screens using the tracked gaze point of the first eye;
  determining a corresponding region in the second one of the right and left two-dimensional display screens using the tracked gaze point of the first eye and the global offset; and
  determining a region offset by comparison of the regions in the first and second ones of the right and left two-dimensional display screens.

6. The method of claim 3, wherein the determining of the feature offset of corresponding features of the right and left stereo images comprises:
  identifying features proximal to the tracked gaze point of the first eye in the determined region in the first one of the right and left two-dimensional display screens;
  identifying corresponding features in the determined corresponding region in the second one of the right and left two-dimensional display screens; and
  determining a feature offset indicative of the gaze point of the second eye on the second one of the right and left two-dimensional display screens using the locations of the identified corresponding features.

7. The method of claim 3, wherein the estimating of the gaze point of the second eye of the user on the second one of the right and left two-dimensional display screens includes determining which one of the region offset, the feature offset, the interpolation of previously determined and prior-in-time gaze points of the second eye of the user, and the global offset is to be used for the estimation by:
  determining a first confidence score indicative of a reliability of the region offset determination;
  determining whether the first confidence score is greater than a first threshold value; and
  if the first confidence score is determined to be greater than the first threshold value, then using the region offset, otherwise, using one of the feature offset, the interpolation of previously determined and prior-in-time gaze points of the second eye of the user, and the global offset.

8. The method of claim 7, wherein the determining of which one of the region offset, the feature offset, the interpolation of previously determined and prior-in-time gaze points of the second eye of the user, and the global offset is to be used for the estimation further comprises:
  if the first confidence score is determined not to be greater than the first threshold value, then determining whether the first confidence score is greater than a second threshold value which is less than the first threshold value;
  if the first confidence score is determined to be greater than the second threshold value, then using one of the feature offset, the interpolation of previously determined and prior-in-time gaze points of the second eye of the user, and the global offset; and
  if the first confidence score is determined not to be greater than the second threshold value, then using one of the interpolation of previously determined and prior-in-time gaze points of the second eye of the user, and the global offset according to the availability and a reliability of the previously determined and prior-in-time gaze points of the second eye of the user.

9. The method of claim 8, wherein if the first confidence score is determined not to be greater than the first threshold value, but greater than the second threshold value, then using the feature offset to estimate the gaze point of the second eye of the user on the second one of the right and left two-dimensional display screens.

10. The method of claim 8, wherein if the first confidence score is determined not to be greater than the first threshold value, but greater than the second threshold value, then
  determining a second confidence score indicative of a reliability of the feature offset determination,
  determining whether the second confidence score is greater than the second threshold value,
  if the second confidence score is determined to be greater than the second threshold value, then using the feature offset, and
  if the second confidence score is determined not to be greater than the second threshold value, then using one of the interpolation of previously determined and prior-in-time gaze points of the second eye of the user, and the global offset according to the availability and the reliability of the previously determined and prior-in-time gaze points of the second eye of the user.

11. The method of claim 3, wherein the estimating of the gaze point of the second eye of the user on the second one of the right and left two-dimensional display screens is subject to one or more of a soft epi-polar constraint, a focus constraint, or a depth constraint.

12. The method of claim 2, wherein the estimation of the three-dimensional gaze point is based upon relative contributions of the tracked gaze point of the first eye on the first one of the two-dimensional display screens and the estimated gaze point of the second eye on the second one of the two-dimensional display screens, wherein the relative contributions depend upon a confidence score for the tracking of the gaze point of the first eye of the user on the first one of the right and left two-dimensional display screens.

13. The method of claim 2, further comprising:
tracking a gaze point of the second eye of the user on the second one of the right and left two-dimensional display screens;
estimating a gaze point of the first eye of the user on the first one of the right and left two-dimensional display screens by processing information of the tracked gaze point of the second eye and the information of the right and left stereo images of the scene; and
estimating the three-dimensional gaze point using the tracked and estimated gaze points of the first and second eyes of the user by adjusting the contributions of the tracked and estimated gaze points of the first and second eyes of the user according to tracking confidence scores for tracking the gaze points of the first and second eyes on the first and second ones of the right and left two-dimensional display screens.

14. The method of claim 13, wherein the three-dimensional gaze point is estimated using the tracked and estimated gaze points of the first and second eyes of the user by adjusting the contributions of the tracked and estimated gaze points of the first and second eyes of the user according to the tracking confidence scores and estimation confidence scores for estimating the gaze points of the first and second eyes on the first and second ones of the right and left two-dimensional display screens.

15. A system comprising:
a stereo viewer having right and left two-dimensional display screens disposed so as to align with right and left eyepieces that align with right and left eyes of a user, wherein the right and left two-dimensional display screens respectively display information of right and left stereo images of a scene captured by a stereoscopic camera;
a first tracking system having a first single-eye tracker configured to track a gaze point of a first eye of the user through one of the right and left eyepieces on a first one of the right and left two-dimensional display screens; and
a processor configured to estimate a gaze point of a second eye of the user on a second one of the right and left two-dimensional display screens by processing information of the tracked gaze point of the first eye only and the information of the right and left stereo images of the scene.

16. The system of claim 15, wherein the processor is configured to estimate a three-dimensional gaze point using the tracked gaze point of the first eye and the estimated gaze point of the second eye of the user.

17. The system of claim 15, wherein the processor is configured to process the information of the tracked gaze point of the first eye and the information of the right and left stereo images of the scene by:

determining one or more of a global offset of the right and left stereo images, a region offset of corresponding regions of the right and left stereo images using the global offset and the tracked gaze point of the first eye, or a feature offset of corresponding features within the corresponding regions of the right and left stereo images; and
estimating the gaze point of the second eye of the user on the second one of the right and left two-dimensional display screens by using one of the region offset, the feature offset, an interpolation of previously determined and prior-in-time gaze points of the second eye of the user, and the global offset according to a reliability of at least one of the determinations and an availability of the previously determined and prior-in-time gaze points of the second eye of the user.

18. The system of claim 15, wherein the processor is configured to estimate the three-dimensional gaze point based upon relative contributions of the tracked gaze point of the first eye on the first one of the two-dimensional display screens and the estimated gaze point of the second eye on the second one of the two-dimensional display screens, wherein the relative contributions depend upon a confidence score for the tracking of the gaze point of the first eye of the user on the first one of the right and left two-dimensional display screens.

19. The system of claim 16, further comprising:
a second tracking system having a second single-eye tracker for tracking a gaze point of the second eye of the user on the second one of the right and left two-dimensional display screens;
wherein the processor is configured to:
estimate a gaze point of the first eye of the user on the first one of the right and left two-dimensional display screens by processing information of the tracked gaze point of the second eye and the information of the right and left stereo images of the scene, and
estimate the three-dimensional gaze point using the tracked and estimated gaze points of the first and second eyes of the user by adjusting contributions of the tracked and estimated gaze points of the first and second eyes of the user according to tracking confidence scores for tracking the gaze points of the first and second eyes on the first and second ones of the right and left two-dimensional display screens.

20. The system of claim 19, wherein the processor is configured to estimate the three-dimensional gaze point using the tracked and estimated gaze points of the first and second eyes of the user by adjusting the contributions of the tracked and estimated gaze points of the first and second eyes of the user according to the tracking confidence scores and estimation confidence scores for estimating the gaze points of the first and second eyes on the first and second ones of the right and left two-dimensional display screens.

* * * * *